United States Patent
Ryoo et al.

(10) Patent No.: US 10,682,370 B2
(45) Date of Patent: Jun. 16, 2020

(54) TOPICAL ANTIVIRAL COMPOSITION CONTAINING A LOCAL ANESTHETIC AND METHOD OF MAKING THE SAME

(71) Applicant: NAL PHARMACEUTICALS, LTD., Hong Kong (CN)

(72) Inventors: Je Phil Ryoo, Princeton, NJ (US); Chun Kwong Chu, Hong Kong (CN)

(73) Assignee: NAL PHARMACEUTICAL GROUP LIMITED, Hong Kong (CN)

( * ) Notice: Subject to any disclaimer, the term of this patent is extended or adjusted under 35 U.S.C. 154(b) by 79 days.

(21) Appl. No.: 14/774,627

(22) PCT Filed: Mar. 12, 2014

(86) PCT No.: PCT/US2014/024919
§ 371 (c)(1),
(2) Date: Sep. 10, 2015

(87) PCT Pub. No.: WO2014/159731
PCT Pub. Date: Oct. 2, 2014

(65) Prior Publication Data
US 2016/0015731 A1    Jan. 21, 2016

Related U.S. Application Data

(60) Provisional application No. 61/780,041, filed on Mar. 13, 2013.

(51) Int. Cl.
| | | |
|---|---|---|
| *A61K 31/7072* | (2006.01) |
| *A61K 9/00* | (2006.01) |
| *A61K 45/06* | (2006.01) |
| *A61K 31/167* | (2006.01) |
| *A61K 9/06* | (2006.01) |
| *A61K 47/14* | (2017.01) |
| *A61K 47/02* | (2006.01) |
| *A61K 47/10* | (2017.01) |
| *A61K 47/16* | (2006.01) |
| *A61K 47/26* | (2006.01) |
| *A61K 47/32* | (2006.01) |
| *A61K 47/38* | (2006.01) |
| *A61K 47/42* | (2017.01) |

(52) U.S. Cl.
CPC ........ *A61K 31/7072* (2013.01); *A61K 9/0014* (2013.01); *A61K 9/06* (2013.01); *A61K 31/167* (2013.01); *A61K 45/06* (2013.01); *A61K 47/02* (2013.01); *A61K 47/10* (2013.01); *A61K 47/14* (2013.01); *A61K 47/16* (2013.01); *A61K 47/26* (2013.01); *A61K 47/32* (2013.01); *A61K 47/38* (2013.01); *A61K 47/42* (2013.01)

(58) Field of Classification Search
None
See application file for complete search history.

(56) References Cited

U.S. PATENT DOCUMENTS

| 5,411,738 A | * | 5/1995 | Hind | ..... | A61K 9/0014 |
| | | | | | 424/443 |
| 7,618,950 B2 | * | 11/2009 | Yamamoto | ..... | A61K 31/7056 |
| | | | | | 514/49 |
| 2002/0048798 A1 | * | 4/2002 | Avery | ..... | C07C 323/52 |
| | | | | | 435/183 |

FOREIGN PATENT DOCUMENTS

| CN | 101628116 A | * | 1/2010 | ..... A61K 45/06 |
| JP | H06247879 A | * | 9/1994 | ..... A61K 47/10 |
| RU | 2438697 C1 | * | 1/2012 | ..... A61K 31/167 |
| WO | WO 1993000114 A | * | 1/1993 | ..... A61K 45/06 |
| WO | WO 2010020789 A2 | * | 2/2010 | |

OTHER PUBLICATIONS

Gnann, J. W., Crumpacker, C. S., Lalezari, J. P., Smith, J. A., Tyring, S. K., Baum, K. F., . . . & Cloud, G. A. (1998). Sorivudine versus acyclovir for treatment of dermatomal herpes zoster in human immunodeficiency virus-infected patients: results from a randomized, controlled clinical trial. Antimicrobial agents and chemotherapy, 42(5), 1139-1145.*

"2,6-Di-Tert-Butyl-4-Methoxyphenol" spec sheet retrieved from https://www.chemicalbook.com/ChemicalProductProperty_EN_CB1755853.htm on Oct. 11, 2019 (Year: 2019).*

* cited by examiner

*Primary Examiner* — Dale R Miller
(74) *Attorney, Agent, or Firm* — Lucas & Mercanti, LLP

(57) ABSTRACT

The present invention provides a novel pharmaceutical composition and method of making the same. The composition comprises an effective amount of an antiviral agent and a local anesthetic. The antiviral drug can be sorivudine. The local anesthetic can be lidocaine or its pharmaceutically acceptable salt. Herpes virus infections in humans can be caused by different human herpes viruses, the most common being herpes simplex virus types 1 and 2 (HSV1 and HSV2) and varicella-zoster virus (VZV).

6 Claims, No Drawings

TOPICAL ANTIVIRAL COMPOSITION CONTAINING A LOCAL ANESTHETIC AND METHOD OF MAKING THE SAME

CROSS-REFERENCE TO RELATED APPLICATION

This application is a 371 of PCT/US2014/024919 filed Mar. 12, 2014, which claims the benefit of priority from U.S. Provisional Patent Application Ser. No. 61/780,041 filed Mar. 13, 2013, the contents of which are incorporated herein by reference.

FIELD OF THE INVENTION

The present invention relates to a pharmaceutical composition and method of making the same. More particularly, the present invention relates to topical composition containing an antiviral agent and a local anesthetic.

BACKGROUND OF THE INVENTION

Herpes virus infections in humans can be caused by different human herpes viruses, the most common being herpes simplex virus types 1 and 2 (HSV1 and HSV2) and varicella-zoster virus (VZV).

Following a primary infection with herpes simplex virus or varicella-zoster virus, the virus establishes latency in the sensory nerve cells for the rest of the patient's life and can subsequently be reactivated repeatedly. Following a reactivation in the nerve cell, the virus is transported through the nerves to the skin and subsequently a lesion develops. One characteristic of herpes virus infection is the inflammation which follows immediately upon an outbreak of virus replication. The inflammation contributes to all symptoms associated with herpes virus recurrence including redness, swelling, itching and pain as well as lesions.

Orofacial lesions, commonly known as fever blisters or cold sores, are caused by HSV1. These lesions most commonly appear on the lips, but may appear on the face, in the mucous membrane lining of the oral cavity, in the eye and nose, and occasionally on the trunk of hands. Infections of the mouth, herpes labialis, are called cold sore (feverblister). Other parts of the face can also be affected and the infections thereof are referred to as facial herpes simplex. The infection can also manifest itself on other parts of the body.

Genital HSV infections are most often caused by HSV-2 and following the primary infection the virus will latently infect sensory or autonomic ganglions. Reactivation will produce the local recurrent lesions on or near the genitals that are characteristic of the herpes infection.

Varicella-zoster virus (VZV) causes varicella, commonly known as chicken pox, and herpes zoster, commonly known as shingles. Shingles affects the skin and nerves and is characterized by groups of small blisters or lesions appearing along certain nerve segments. The lesions are most often seen on the back and may be preceded by a dull ache in the affected site. Pain typically occurs approximately 1 to 3 days before the onset of the rash, but may precede it by a week or more. Once the characteristic unilateral dermatomal rash appears, the diagnosis is almost certain. This rash begins as erythematous macules and papules, which progress first to vesicles (within 12-24 hours), then the pustules (in 3-4 days), and finally to crusts (in 7-10 days).

Once an individual has been infected with the herpes virus, the virus will thereafter remain latently in the body. In latent state, the virus is situated in nerve cell bodies in the ganglia. Due to particular stimuli, such as influenza infection, other respiratory disorders, gastrointestinal infections, stress, fatigue, menstruation, pregnancy, allergy, sunlight, or fever, the latent virus can be activated and travel from the ganglia along the well-defined nerve paths to the skin surface and there multiply and cause the symptoms.

There are a number of antiviral agents which are active against the herpes viruses. Most of the available treatments can only help to accelerate the healing of the lesions and the associated symptoms.

Currently, acyclovir, idoxuridine, famciclovir, vidarabine, foscarnet, valacyclovir, and interferon alpha have all been shown to be efficacious in treating VZV infections. Acyclovir, 9-(2-hydroxyethoxymethyl), Zovirax® Ointment (Glaxo Wellcome), is a purine nucleoside analogue targeting viral encoded DNA polymerase. Other purine nucleoside analogues which are commercially available for treating herpes virus infections include ganciclovir (Roche), penciclovir (Novartis) and foscarnet (Astra). Although effective, these purine nucleoside analogues are poorly soluble in water and demonstrate low bioavailability. These, accompanying the relative long recovery time required (i.e., generally takes longer than 2 weeks for patients to recover).

In the management of pain and discomfort, local anesthetics are widely used. Local anesthetics reversibly block the impulse conduction along nerves and other excitable membranes that primarily utilize sodium channels. Clinically, this action blocks the pain sensation from specific areas of the body.

Among the local anesthetics, lidocaine, 2-(diethylamino)-N-(2,6-dimethylphenyl)-acetamide, is particularly known for its treatment of ventricular tachycardia (an arrythmia of the heart) as an intravenous injection solution. (See e.g., U.S. Pat. No. 3,968,205). Lidocaine is also widely used as a vasoconstrictor to reduce regional blood flow in topical applications or aerosols (such as nasal aerosols to reduce nasal congestion). (See e.g., U.S. Pat. No. 5,534,242). In addition, lidocaine is known for its therapeutic effects in reducing post-herpetic neuralgia (PHN) nerve injury pain from shingles (herpes zoster and post herpetic neuralgia) and analogous neuropathies. For example, U.S. Pat. No. RE37,727 discloses methods employing lidocaine intradermal administration by transport lidocaine from the skin surface, using patches and dressings, into the skin.

There is a great need for effective drugs and methods of treatment for recurrent herpes infections. The present invention addresses this need.

SUMMARY OF INVENTION

A pharmaceutical composition containing an antiviral agent and a local anesthetic is provided. The composition comprises an effective amount of an anti-viral drug and a local anesthetic.

Antiviral substances can be selected from a group comprising compounds acting on viral DNA polymerase, such as nucleoside analogues after phosphorylation to their triphosphate forms; phosphonoformic and phosphonoacetic acids and their analogues; and other antiviral compounds having a different mechanism of action. As examples of antiviral substances which can be used in the combination of the invention can be mentioned acyclovir (ACV), ACV-phosphonate, brivudine (bromovinyldeoxyuridine, BVDU), carbocyclic BVDU, buciclovir, CDG (carbocyclic 2'-deoxyguanosine), cidofovir (HPMPC, GS504), cyclic HPMPC, desciclovir, edoxudine, famciclovir, ganciclovir (GCV), GCV-phosphonate, genivir (DIP-253), H2G (9-[4-hydroxy- 2-(hydroxymethyl)butyl]guanine), HPMPA, lobucavir (bis-hydroxymethylcyclobutylguanine, BHCG), netivudine (zonavir, BW882C87), penciclovir, PMEA (9-(2-phosphonylmethoxy-ethyl)adenine), PMEDAP, sorivudine (brovavir, BV-araU), valacyclovir, 2242 (2-amino-7-(1,3-dihydroxy-2-propoxymethyl)purine), HOE 602, HOE 961; BPFA (batyl-PFA), PAA (phosphonoacetate), PFA (phosphonoformate); arildone, amantadine, BILD 1263, civamide (capsaicin), CRT, ISIS 2922, peptide T, tromantadine, virend, 1-docosanol (lidakol) and 348U87 (2-acetylpyridine-5-[2-chloro-anilino-thiocarbonyl]-thiocarbonohydrazone).

Further examples of antiviral substances include those with specific antiviral activity such as herpes specific nucleoside analogues which are preferentially phosphorylated in virus-infected cells and have very low or non-existent incorporation into cellular DNA as well as other compounds with specific antiviral activity. Acyclovir, for instance, has a selectivity ratio for the inhibitory activity against HSV-1 in vitro of about 2000. Among said substances can be mentioned brivudine, cidofovir, desciclovir, famciclovir, ganciclovir, HOE 961, lobucavir, netivudine, penciclovir, PMEA, sorivudine, valacyclovir, 2242, BPFA, PFA, PAA.

The antiviral drug can be acyclovir, peniclovir, ganciclovir, a prodrug thereof or a mixture thereof. Antiviral substances suitable for the purposes of the present invention are topically acceptable antiviral compounds which in addition to being specific inhibitors of herpes virus multiplication also are active after topical administration and in addition pharmaceutically acceptable for topical administration. This means that the toxicity of the antivirals must be sufficiently low to allow for a continuous contact with the human body and in particular with the skin and mucous membranes.

A preferred antiviral drug can be sorivudine. Sorivudine is a nucleoside analogue that was investigated for the treatment of VZV infections. There was a trend favoring sorivudine for cessation of new vesicle formation, and where the time to total lesion crusting was diminished. However, major toxicity (myelosuppression) occurs if sorivudine is administered concurrently with 5-fluorouracil (5-FU), a drug taken by many patients suffering from herpes virus infection. A metabolite of sorivudine inhibits an enzyme (dihydropyrimidine dehydrogenase) that is required in the metabolization of 5-fluorouracil, causing toxic levels to accumulate Local anesthetics, which may also be incorporated as desired to ease pain, include, without limitation, benoxinate, benzocaine, bupivocaine, butamben, chloroprocaine, cocaine, diamocaine, dibucaine, dyclonine, ethyl chloride, etidocaine, euprocin, isobutamben, lidocaine, mepevicaine, oxethazine, pramoxine, prilocaine, pyrocaine, risocaine, rodocaine, tetracaine, and mixtures thereof; preferably benzocaine, lidocaine, tetracaine, and mixtures thereof). A preferred local anesthetic can be lidocaine or its pharmaceutically acceptable salt.

A method of treating skin of a patient with pain and/or inflammation associated with lesions/blisters by herpes virus or enterovirus is also provided. The method comprises steps of topically applying a topical composition to the skin of the patient to decrease at least one of the following: lesion number on the skin, total lesion area on the skin, and the virus titer, where the topical composition comprises an effective amount of an anti-viral drug and a local anesthetic, where the antiviral drug can be sorivudine and the local anesthetic can be lidocaine or its pharmaceutically acceptable salt.

It is to be understood that both the foregoing general description and the following detailed description are by examples, and are intended to provide further explanation of the invention as claimed.

DETAILED DESCRIPTION OF INVENTION

The present invention provides a novel pharmaceutical composition comprising an effective amount of an antiviral agent and a local anesthetic.

Furthermore, the present invention provides a pharmaceutical composition for topical administration consisting of an antiviral drug; and a local anesthetic.

In the treatment of herpes with sorivudine, it is well known to take 5 to 7 days for the antiviral agent to take effect. Thus, most of the patients would not tolerate the severe pain and itchiness in the infected site of the skin resulting from the herpetic infection. Therefore, a monotherapy using only an antiviral agent such as sorivudine could not successfully treat the patients.

In the present invention, an improved combination therapy is developed by applying both sorivudine and lidocaine thereby successfully treating herpes patients, where lidocaine will effectively relieve pain/itchiness resulting from the herpetic infection during the 5 to 7 day-delay of effective treatment with sorivudine.

The present invention allows for the topical application of the pharmaceutical composition comprising the antiviral agent sorivudine and the local anesthetic lidocaine or its pharmaceutically acceptable salt in herpes patients taking 5-FU. Since the composition is applied topically, e.g., patch or cream, the adverse reaction of drug-to-drug interaction is avoided, thus, avoiding potential cause of death.

Moreover, the present invention provides for the optimal formulation pH range for the pharmaceutical composition comprising the antiviral agent sorivudine and the local anesthetic lidocaine or its pharmaceutically acceptable salt.

According to an embodiment of the present invention, there is provided a pharmaceutical composition for topical administration comprising an antiviral drug and a local anesthetic, where the antiviral drug can be sorivudine and the local anesthetic can be lidocaine or its pharmaceutically acceptable salt.

In another embodiment, the pharmaceutical composition according to the invention, the pH of the composition can be from about 2.0 to about 9.5 or about 2.0 to about 7.0, or the pH of the composition is from about 3.0 to about 6.0, or alternatively, the pH of the composition is from about 4.0 to about 5.0.

In the pharmaceutical composition according to the invention, the range of the antiviral drug sorivudine is from about 1% to about 5%, or from about 2% to about 4%, or alternatively, the antiviral drug can be sorivudine 3%.

In a further embodiment, the range of the local anesthetic lidocaine or its pharmaceutically acceptable salt of the pharmaceutical composition according to the invention, is from about 1% to about 6%, or from about 2% to about 5%, or alternatively from about 4% to about 6%, or even from about 2% to about 4%.

In a preferred embodiment, the local anesthetic is 2% lidocaine or its pharmaceutically acceptable salt. In another preferred embodiment, the local anesthetic is 4% lidocaine or its pharmaceutically acceptable salt. In a further preferred embodiment, the local anesthetic is 5% lidocaine or its pharmaceutically acceptable salt.

In the pharmaceutical composition of the invention, the ratio of the amount of the antiviral drug and the local anesthetic is from about 1:5 to about 5:1 by weight.

In a preferred embodiment of the invention, there is provided a pharmaceutical composition wherein the antiviral drug is sorivudine 5% and the local anesthetic is lidocaine 5%.

In another preferred embodiment of the invention, there is provided a pharmaceutical composition wherein the antiviral drug is sorivudine 3% and the local anesthetic is lidocaine 5%.

In a particularly preferred embodiment, there is provided a pharmaceutical composition wherein the antiviral drug is sorivudine 3% and the local anesthetic is lidocaine 2%.

In another particularly preferred embodiment, there is provided a pharmaceutical composition wherein the antiviral drug is sorivudine 3% and the local anesthetic is lidocaine 5%.

The present invention also provides for a pharmaceutical composition for topical administration comprising an antiviral drug and a local anesthetic, where the antiviral drug can be sorivudine and the local anesthetic can be lidocaine or its pharmaceutically acceptable salt and further comprising an excipient.

The excipient can be selected from among antioxidant, surfactant, humectant, solubilizer, solvent, base polymer, emulsifier, diluent, and pH adjusters.

A surfactant can be selected from anionic, cationic, nonionic, amphoteric and mixture of surfactants and also from among saturated and unsaturated higher aliphatic acid salts (e.g., sodium laurate, sodium stearate, sodium oleate, sodium linolenate, etc), long-chain alkyl sulfate salts, alkylbenzenesulfonic acids (e.g., hexylbenzenesulfonic acid, octylbenzenesulfonic acid, dodecylbenzenesulfonic acid, etc) and their salts, polyoxyalkylene alkyl ether sulfate salts, polyoxyalkylene alkenyl ether sulfate salts, the salts of polyoxyethylene alkyl sulfate esters, the salts of the alkyl esters of sulfosuccinic acid, polyoxyalkylene sulfosuccinate salts, the salts of the alkyl esters of polyoxyalkylene sulfosuccinic acid, the alkali metal salts of the polyoxyalkylene-modified dimethylpolysiloxane esters of sulfosuccinic acid, polyoxyalkylene alkylphenyl ether sulfate salts, long-chain alkanesulfonic acid salts, long-chain alkylsulfonates, polyoxyethylene alkylphenyl ether sulfate salts, polyoxyalkylene alkyl ether acetate salts, long-chain alkyl phosphate salts, polyoxyalkylene alkyl ether phosphate salts, acylglutamate salts, alpha-acylsulfonate salts, long-chain alkylsulfonate salts, alkylarylsulfonate salts, long-chain alpha-olefinsulfonate salts, alkylnaphthalenesulfonate salts, long-chain alkanesulfonic acid salts, long-chain alkyl or alkenyl sulfate salts, long-chain alkylamide sulfate salts, long-chain alkyl or alkenyl phosphate salts, alkylamide phosphate salts, alkyloylalkyltaurate salts, N-acylamino acid salts, sulfosuccinate salts, alkyl alkyl ether carboxylate salts, amide ether carboxylate salts, the salts of esters of alpha-sulfofatty acids, alanine derivatives, glycine derivatives, and arginine derivatives; salts can be exemplified by alkali-metal salts such as the sodium salt and potassium salt, alkanolamine salts such as the triethanolamine salt, and the ammonium salt, the sodium salt; alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, octyltrimethylammonium hydroxide, dodecyltrimethylammonium hydroxide, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2EO) chloride, benzalkonium chloride, alkylbenzalkonium chloride, alkyldimethylbenzalkonium chloride, benzethonium chloride, stearyldimethylbenzylammonium chloride, lanolin-derived quaternary ammonium salts, diethylaminoethylamide of stearic acid, dimethylaminopropylamide of stearic acid, behenamidopropyldimethylhydroxypropylammonium chloride, stearoylcolaminoformylmethylpyridinium chloride, cetylpyridinium chloride, tall oil alkylbenzylhydroxyethylimidazolinium chloride, and benzylammonium salts; phospholipids, such as lecithin, phosphatidylethanolamine, phosphatidic acid, phosphatidylinositol, phosphatidylserine, phosphatidylcholine, phosphatidylglycerol, sphingomyelin, and cardiolipin, and the hydrogenates of the preceding. Particularly preferred are the hydrogenated natural lecithins as yielded by the hydrogenation of, for example, soy lecithin, egg yolk lecithin, corn lecithin, cottonseed oil lecithin, rapeseed lecithin; polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkylphenols, polyoxyalkylene alkylphenyl ethers, polyoxyalkylenephenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkyl glucosides, polyoxyalkylene fatty acid bisphenyl ethers, polypropylene glycol, polyether-modified silicones (e.g., polyoxyalkylene-modified diorganopolysiloxanes, polyglycerol-modified silicones, glycerol-modified silicones, saccharide-modified silicones), perfluoropolyether-type surfactants, polyoxyethylenepolyoxypropylene block copolymers, and alkyl polyoxyethylenepolyoxypropylene block copolymer ethers.

A humectant can be selected from among sorbitol, mineral oil, vegetable oil and glycerol; betaine, guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof; collagen, gelatin, aloe vera, hyaluronic acid or volatile water-soluble solvents, for instance ethanol or propylene glycol.

A solubilizing agent can be selected from among citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEEN® and spans, e.g., TWEEN 80®; polyoxyethylene sorbitan fatty acid ester, polyoxyethylene n-alkyl ethers, n-alkyl amine n-oxides, polyoxamers, organic solvents, such as acetone, phospholipids, cyclodextrin, triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200 to 600, glycofurol, transcutol, propylene glycol, and dimethyl isosorbide, miglyol, glycerin and glycerol.

A solvent can be selected from among methylene chloride, beta-cyclodextrin, dichloromethane; oily excipients or solvents are vegetable or animal oils, such as sunflower oil or cod liver oil; for aqueous or alcoholic solutions are water, ethanol, sugar solutions, or mixtures thereof; physiological saline solution or alcohols, e.g. ethanol, propanol, glycerol, in addition also sugar solutions such as glucose or mannitol solutions, or mixtures thereof; isopropyl alcohol; aromatic hydrocarbon solvents such as toluene and xylene; ether solvents such as dioxane and THF; aliphatic hydrocarbon solvents; ester solvents; ketone solvents; chlorinated hydrocarbon solvents; dichloromethane, chloroform, 1,2-dichloroethane, diethyl ether, tert-butylmethyl ether, acetonitrile, ethyl acetate, 1,3-dimethyl-2-imidazolidinone, tetrahydrofuran, dimethylformamide, benzene, toluene, xylene, N-dimethylacetamide, N-methylpyrrolidine, chlorobenzene, dimethylsulfoxide, dimethoxyethane, water, methanol, ethanol, isopropanol, pyridine, nitromethane, mixtures thereof.

A base polymer can be selected from among polysaccharide-based polymers, such as guar, xanthan and/or their derivatives; hydrophobic base polymers such as SIS (styrene/isoprene/styrene)-triblock copolymers, SBS (styrene/butadiene/styrene)-triblock copolymers, SBR (copolymers of styrene and butadiene), synthetic and/or natural polyisoprenes, polyamide, polyester, co-polyester, polyurethane, and/or mixtures thereof are also possible as further matrices; water-soluble polymers, plant base polymers such as gum arabic, tragacanth gum, galacian, guar gum, carob gum, karaya gum, carragbeein, pectin, agar, quince seed (Marumero) algae colloid (seaweed extract), starch (rice, corn, potato, wheat), glycyrrhinic acid; microorganism base polymers such as xanthane gum, dextran, succinoglutan, pullulan; animal base polymers such as collagen, caseine, albumin, gelatin; starch base polymers such as carboxymethyl starch, methythydroxypropyl starch; cellulose base polymers such as methyl cellulose nitro cellulose, ethyl cellulose, methythydroxypropyl cellulose, hydroxyethyl cellulose, sodium cellulose sulfate, hydroxypropyl cellulose, sodium carboxymethyl cellulose (CMC), crystalline cellulose, cellulose powder; alginate base polymers such as sodium alginate, alginate propylene glycol esters; vinyl base polymers such as a polyvinyl alcohol, polyvinylmethyl ether, polyvinylpyrrolidone carboxyvinyl polymer (Carbopol), alkyl modified carboxyvinyl polymer, polyoxyethylene base polymers such as polyethylene glycol 2000, 4000, 6000; acryl base polymers such as polyacrylates, a salt of polyacrylate, polyoxyethylene polyoxypropylene copolymer brae polymer, sodium polyacrylate, polyethylene acrylate, polyacryl amide, polyethylene imine, cationic polymer, etc.

An emulsifier can selected from among ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof; carbomer, hydroxypropyl cellulose, sodium lauryl sulfate; glycerin fatty acid esters (monoglycerides, MG); mono- and di-glycerides (MG & DG) (e.g. Grindsted HV 40™, Poem J-2021™); distilled monoglycerides; citric acid esters of MG (CMG); diacetyl tartaric acid esters of mono- and di-glycerides (DATEMs) (e.g. Panodan AL 10™); polyglycerol esters of fatty acids (PGE); polyglycerol polyricinoleate (PGPR); sorbitan esters of fatty acids (e.g. Palsgaard 7463™); sucrose esters of fatty acids; calcium stearoyl lactylates; sodium stearoyl lactylates; lecithin (including enzyme digested lecithin); and caseinates (such as sodium caseinates including Alanate 191™); diacetyl tartaric acid esters of mono- and di-glycerides (DATEMs).

A diluent can be selected from among water, saline, finger's solutions, dextrose solution; calcium carbonate, sodium carbonate, lactose, calcium phosphate or sodium phosphate; granulating and disintegrating agents, e.g., corn starch or alginic acid; binding agents, for example starch gelatin, acacia, microcrystalline cellulose or polyvinyl pyrrolidone; dicalcium phosphate, calcium sulfate, lactose, sorbitol, sucrose, inositol, cellulose, kaolin, mannitol, sodium chloride, dry starch, and powdered sugar.

pH adjustments can be made using organic or inorganic acid/base such as dilute HCl and dilute phosphoric acid, citric acid or dilute NaOH and triethanolamine (TEA). Those with ordinary skill in the art can appreciate that the abbreviation q.s. is often used to indicate that liquid is added to given final volume. For example, pH can be adjusted with purified water to q.s. (quantum satis or quantum sufficient).

In a preferred embodiment, there is provided a pharmaceutical composition for topical administration comprising an antiviral drug and a local anesthetic, where the antiviral drug is sorivudine and the local anesthetic is lidocaine or its pharmaceutically acceptable salt and further comprising an excipient, wherein the excipient is an anti-oxidant.

An anti-oxidant can be selected from among sodium bisulfite, butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

In another preferred embodiment, there is provided a pharmaceutical composition wherein the anti-oxidant is BHT or sodium bisulfite.

The present invention provides for a cream for topical administration comprising an antiviral drug and a local anesthetic wherein,
the pH of the composition is from about 2.0 to about 9.5;
the antiviral drug is sorivudine and has a range of from about 1% to about 5%;
the local anesthetic is lidocaine or its pharmaceutically acceptable salt and has a range of from about 1% to about 6%; and
the ratio of the amount of the antiviral drug and the local anesthetic is from about 3:2 to about 3:5 by weight %.

The present invention also provides a patch comprising an antiviral drug and a local anesthetic wherein,
the pH of the composition is from about 4.0 to about 7.0;
the antiviral drug is sorivudine and has a range of from about 1% to about 5%;
the local anesthetic is lidocaine or its pharmaceutically acceptable salt and has a range of from about 1% to about 6%; and
the ratio of the amount of the antiviral drug and the local anesthetic is from about 3:2 to about 3:5 by weight %.

In a certain embodiment, in the patch according to the present invention, the local anesthetic is lidocaine or its pharmaceutically acceptable salt and has a range of from about 2% to about 5%.

In another embodiment, in the patch according to the present invention, the local anesthetic is lidocaine or its pharmaceutically acceptable salt and has a range of from about 4% to about 6%.

In a further embodiment, in the patch according to the present invention, the local anesthetic is lidocaine or its pharmaceutically acceptable salt and is about 5%.

The present invention further provides for an ointment comprising an antiviral drug and a local anesthetic wherein,
the pH of the composition is from about 4.0 to about 7.0;

the antiviral drug is sorivudine and has a range of from about 1% to about 5%;

the local anesthetic is lidocaine or its pharmaceutically acceptable salt and has a range of from about 2% to about 4%; and the ratio of the amount of the antiviral drug and the local anesthetic is from about 3:2 to about 3:5 by weight %.

The present invention also provides a method for treating herpes virus infections of the skin and pain associated therewith comprising topically applying any one of the pharmaceutical compositions described above.

There is also provided a cream, lotion, gel or ointment, solution, liniment, suspension, lacquer, or spray containing any one of the pharmaceutical compositions described above.

Any of the above described pharmaceutical compositions can be contained in a topical patch, transdermal patch, hydrogel patch, matrix patch, reservoir patch, electrophoresis patch and micro-needle patch Some preparation examples (gel, cream, ointment or patch formulation) of the pharmaceutical acceptable composition described above are disclosed below. These examples are illustrative, but not limiting the scope of the present invention. Reasonable variations, such as those occur to reasonable artisan, can be made herein without departing from the scope of the present invention.

EXAMPLES

Examples 1-7

The patch formulations containing Sorivudine and Lidocaine were prepared as follows:

Example 1

Base mixture: Polyacrylate in purified water was mixed with polysorbate 80, gelatin, D-sorbitol to obtain Mixture 1. A solution of lidocaine and sorivudine in propylene glycol and diethylene glycol monoethyl ether was added to Mixture 1 and stirred until all of the active ingredients were dissolved to obtain Mixture 2. Then, to Mixture 2 a dispersion of sodium polyacrylate, carboxylmethylcellulose sodium, titanium dioxide, dihydroxyalumium aminoacetate, methyl paraban and propyl paraban in glycerin was added, sufficiently agitated until a uniform mixture was obtained.

Coating Sheet: The Base mixture was applied onto and spread over a release liner and laminated with a non-woven fabric backing film. The coating sheet was cut into desired sizes to give a topical preparation for the skin having a pH value of 6~8 and containing 2 mg/cm$^2$ of lidocaine and 3 mg/cm$^2$ of sorivudine.

Example 2

Base mixture: Polyacrylate in purified water was mixed with polysorbate 80, gelatin, D-sorbitol to obtain Mixture 1. A solution of lidocaine and sorivudine in propylene glycol and diethylene glycol monoethyl ether was added to Mixture 1 and stirred until all of the active ingredients were dissolved to obtain Mixture 2. Then, to Mixture 2 a dispersion of carboxylmethylcellulose sodium, titanium dioxide, dihydroxyalumium aminoacetate, methyl paraban and propyl paraban in glycerin was added, and sufficiently agitated until a uniform mixture was obtained.

Coating Sheet: The Base mixture was applied onto and spread over a release liner and laminated with a non-woven fabric backing film. The coating sheet was cut into a desired size to give a topical preparation for the skin having a pH value of 6~8 and containing 2 mg/cm$^2$ of lidocaine and 3 mg/cm$^2$ of sorivudine.

Examples 3-7

Base mixture: Polyacrylate in purified water was mixed with Kaolin, Urea, D-sorbitol to obtain Mixture 1. A solution of lidocaine and sorivudine in propylene glycol was added to Mixture 1 and stirred until all of the active ingredients were dissolved to obtain Mixture 2. Then, to Mixture 2 a dispersion of sodium polyacrylate, carboxylmethylcellulose sodium, dihydroxyalumium aminoacetate, methyl paraban and propyl paraban in glycerin was added, and sufficiently agitated until a uniform mixture was obtained.

Coating Sheet: The Base mixture was applied onto and spread over a release liner and laminated with a non-woven fabric backing film. The coating sheet was cut into a desired size to give a topical preparation for the skin having a pH value of 6~8 and containing 2 mg/cm$^2$ of lidocaine and 3 mg/cm$^2$ of sorivudine.

TABLE 1

Compositions of Sorivudine-Lidocaine patch formulations

| Ingredient | Example 1 | Example 2 | Example 3 | Example 4 | Example 5 | Example 6 | Example 7 |
| --- | --- | --- | --- | --- | --- | --- | --- |
| Lidocaine | 2.00% | 2.00% | 2.00% | 5.00% | 5.00% | 5.00% | 4.00% |
| Sorivudine | 3.00% | 3.00% | 3.00% | 3.00% | 3.00% | 3.00% | 3.00% |
| Na Polyacrylate | 4.00% | 2.00% | 5.00% | 3.00% | 3.00% | 3.00% | 3.00% |
| Polyacrylate | 2.00% | 5.00% | 2.00% | 4.00% | 4.00% | 4.00% | 4.00% |
| Na carboxymethylcellulose | 1.00% | 1.00% | 5.00% | 5.00% | 5.00% | 5.00% | 5.00% |
| Polyviny alcohol | | | 1.00% | 1.00% | 1.00% | 1.00% | 1.00% |
| Gelatin | 1.00% | 1.00% | 1.00% | 1.00% | 1.00% | 1.00% | 1.00% |
| Glycerin | 20.00% | 32.00% | 20.00% | 32.00% | 20.00% | 20.00% | 20.00% |
| Propylene glycol | 5.00% | 5.00% | 5.00% | 5.00% | 5.00% | 5.00% | 5.00% |
| D-sorbitol | 15.00% | 15.00% | 15.00% | 15.00% | 15.00% | 15.00% | 15.00% |
| Diethylene glycol monoethyl ether | 1.00% | 3.00% | 2.00% | 3.00% | 2.00% | 3.00% | 3.00% |
| Polysorbate 80 | 0.30% | 0.30% | 0.30% | 0.30% | | 0.30% | 0.30% |
| Titanium dioxide | 0.20% | | | | | | |
| Urea | | | | 1.00% | 1.00% | 1.00% | 1.00% | 1.00% |
| Kaolin | | | | | 1.00% | | |
| Methyl paraban | 0.10% | 0.10% | 0.10% | 0.10% | 0.10% | 0.10% | 0.10% |
| Propyl paraban | 0.05% | 0.05% | 0.05% | 0.05% | 0.05% | 0.05% | 0.05% |
| Tartaric acid | 2.30% | 1.90% | 1.50% | 0.95% | 1.15% | 0.83% | 2.30% |

TABLE 1-continued

Compositions of Sorivudine-Lidocaine patch formulations

| Ingredient | Example 1 | Example 2 | Example 3 | Example 4 | Example 5 | Example 6 | Example 7 |
| --- | --- | --- | --- | --- | --- | --- | --- |
| Phosporic acid | 0.02% | 0.02% | 0.02% | 0.02% | 0.02% | 0.02% | 0.02% |
| Dihydroxyaluminium amonoacetate | 0.50% | 0.50% | 0.50% | 0.50% | 0.30% | 0.50% | 0.50% |
| EDTA-Na2 | 0.10% | 0.10% | 0.50% | 0.10% | 0.15% | 0.10% | 0.10% |
| Purified water | Q.S. | Q.S. | Q.S. | Q.S. | Q.S. | Q.S. | Q.S. |
| pH | 4.9 | 5.5 | 6.0 | 6.7 | 6.5 | 6.9 | 5.0 |

Examples 8-17

The cream formulations of Examples 8-17 containing Sorivudine and Lidocaine were prepared as follows:

Examples 8 and 15

Solution A: Cetylalcohol, octadecanol, caprylic/capric triglyceride, glyceryl monostearate and dimethicone were weighed and mixed to obtain a mixture. The mixture was heated at 70-80° C. until all components were dissolved.

Solution B: D1811, Tween80, span80, glycerol were dissolved in ethanol at 60-70° C. Lidocaine HCl was dissolved in purified water and then added into Solution B to provide Solution C.

Solution A and Solution C were mixed at 60-80° C. and emulsified for 5-15 minutes to provide a cream. Then Sorivudine was slowly dispersed into the cream and emulsified for 10-15 minutes.

Examples 9 and 14

Solution A: Cetylalcohol, octadecanol, caprylic/capric triglyceride, glyceryl monostearate and dimethicone and BHT were weighed and mixed to obtain a mixture. The mixture was heated at 70-80° C. until all components were dissolved.

Solution B: D1811, Tween80, span80, glycerol were dissolved in ethanol at 60-70° C. Lidocaine HCl was dissolved in purified water and then added into Solution B to provide Solution C.

Solution A and Solution C were mixed at 60-80° C. and emulsified for 5-15 minutes to provide a cream. Then Sorivudine was slowly dispersed into the cream and emulsified for 10-15 minutes.

Examples 10, 11 and 12

Solution A: Cetylalcohol, octadecanol, caprylic/capric triglyceride, glyceryl monostearate and dimethicone and were weighed and mixed to obtain a mixture. The mixture was heated at 70-80° C. until all components were dissolved.

Solution B: D1811, Tween80, span80, glycerol were dissolved in ethanol at 60-70° C. Lidocaine HCl and Sodium Thiosulfate Pentahydrate were dissolved in purified water and then added into Solution B to provide Solution C.

Solution D: Sorvuidine was dissolved in propylene glycol and PEG400, then slowly emulsified.

Solution A and Solution C were mixed at 60-80° C. and emulsified for 5-15 minutes to obtain a cream. Then Solution D was slowly added and emulsified into the cream for 10-15 minutes. pH was adjusted and q.s. with purified water and then emulsified again for 5-10 minutes.

Example 13

Solution A: Cetylalcohol, octadecanol, caprylic/capric triglyceride, glyceryl monostearate and dimethicone and were weighed and mixed to obtain a mixture. The mixture was heated at 70-80° C. until all components were dissolved.

Solution B: D1811, Tween80, span80, glycerol were dissolved in ethanol at 60-70° C. Lidocaine HCl was dissolved in purified water and then added into Solution B to provide Solution C.

Solution A and Solution C were mixed at 60-80° C. and emulsified for 5-15 minutes to obtain a cream. Then Sorivudine was slowly dispersed and emulsified into the cream for 10-15 minutes. pH was adjusted and q.s. with purified water and then emulsified again for 5-10 minutes.

Example 16

Solution A: Cetylalcohol, octadecanol, caprylic/capric triglyceride, glyceryl monostearate and dimethicone were weighed and mixed to obtain a mixture. The mixture was heated at 70-80° C. until all components were dissolved.

Solution B: D1811, Tween80, span80, glycerol were dissolved in ethanol at 60-70° C. Lidocaine was dissolved into Solution B to provide Solution C.

Solution D: Sorvuidine was dissolved in propylene glycol and PEG400.

Solution A and Solution C were mixed at 60-80° C. and emulsified for 5-15 minutes to obtain a cream. Then slowly added Solution D and emulsified into the cream for 10-15 minutes.

Then pH was adjusted and q.s. with purified water and then emulsified again for 5-10 minutes.

Example 17

Solution A: Cetylalcohol, octadecanol, caprylic/capric triglyceride, glyceryl monostearate dimethicone and BHT were weighed and mixed to obtain a mixture. The mixture was heated at 70-80° C. until all components were dissolved.

Solution B: D1811, Tween80, span80, glycerol were dissolved in ethanol at 60-70° C. Lidocaine was dissolved into Solution B to provide Solution C.

Solution A and Solution C were mixed at 60-80° C. and emulsified for 5-15 minutes to obtain a cream. Sorivudine was dispersed slowly into the cream and emulsified for 10-15 minutes. Then pH was adjusted and q.s. with purified water and then emulsified again for 5-10 minutes.

The compositions of Examples 8-17 are listed in Table 2. The stability results of some of the Examples are provided in Tables 3 to 5.

TABLE 2

Compositions of Sorivudine-Lidocaine cream formulations

| Ingredients | Ex 8 | Ex 9 | Ex 10 | Ex 11 | Ex 12 | Ex 13 | Ex 14 | Ex 15 | Ex 16 | Ex 17 |
|---|---|---|---|---|---|---|---|---|---|---|
| Sorivudine | 3% | 3% | 3% | 3% | 3% | 3% | 3% | 3% | 3% | 3% |
| Lidocaine HCl | 2% | 2% | 4% | 4% | 4% | 2% | 2% | 2% | | |
| Lidocaine | | | | | | | | | 2% | 2% |
| D1811 | 0.5% | 0.5% | 0.5% | 0.5% | 0.5% | 0.5% | 0.5% | 0.5% | 0.5% | 0.5% |
| Tween 80 | 0.25% | 0.25% | 0.5% | 0.5% | 0.5% | 0.25% | 0.25% | 0.5% | 0.5% | 0.5% |
| Span80 | 0.25% | 0.25% | 0.5% | 0.5% | 0.5% | 0.25% | 0.25% | 0.5% | 0.5% | 0.5% |
| Glycerol | 3% | 3% | — | — | — | 3% | 3% | 3% | 3% | 3% |
| Ethanol | 8% | 8% | — | — | — | 8% | 8% | 8% | 3% | 3% |
| Water | 68% | 67.5% | 45.3% | 45.3% | 45.3% | 68% | 67.9% | 67.5% | 40.5% | 72.4% |
| Cetylalcohol | 3% | 3% | 1.5% | 1.5% | 1.5% | 3% | 3% | 3% | 3% | 3% |
| Octadecanol | 3% | 3% | 1.5% | 1.5% | 1.5% | 3% | 3% | 3% | 3% | 3% |
| GTCC* | 2% | 2% | 3% | 3% | 3% | 2% | 2% | 2% | 2% | 2% |
| Dimethicone | 2% | 2% | 2% | 2% | 2% | 2% | 2% | 2% | 2% | 2% |
| MSA* | 5% | 5% | 5% | 5% | 5% | 5% | 5% | 5% | 5% | 5% |
| BHT* | — | 0.5% | — | — | — | — | 0.1% | — | — | 0.1% |
| PEG400 | | | 20% | 20% | 20% | | | | 20% | |
| Carboma980 | | | 0.2% | 0.2% | 0.2% | | | | | |
| Sodium thiosulfate pentahydrate | | | 0.5% | 0.5% | 0.5% | | | | | |
| Propylene glycol (PG) | | | 10% | 10% | 10% | | | | 10% | |
| Benzyl alcohol | | | 2% | 2% | 2% | | | | | |
| Peppermint oil | | | 0.5% | 0.5% | 0.5% | | | | | |
| pH | 4.5 | 4.5 | 5.4 | 7.3 | 9.1 | 7.1 | 4.29 | 4.27 | 2.7 | 8.2 |
| pH adjusted | n/a | n/a | adjusted | adjusted | adjusted | adjusted | n/a | n/a | adjusted | adjusted |

*GTCC: caprylic capric triglyceride; MSA: Glyceryl monstearate; BHT: Butylated hydroxytoluene.

TABLE 3

Stability data of Sorivudine/lidocaine cream formulas of Examples 1 and 2 stored in 40° C./75% RH

| Formula | Drug | | 0 (initial) | 1 month | 2 month | 3 month | 6 month |
|---|---|---|---|---|---|---|---|
| Example 8 (pH 4.5) | Sorivudine | (normalized) | 3.18% | 3.26% | 3.21% | 3.17% | 3.12% |
| | | | 100% | 103% | 101% | 100% | 98% |
| | Lidocaine | (normalized) | 2.10% | 2.09% | 2.07% | 2.13% | 2.13% |
| | | | 100% | 99% | 99% | 102% | 102% |
| Example 9 (pH 4.5) | Sorivudine | (Normialized) | 3.17% | 3.18% | 3.31% | 3.16% | 3.16% |
| | | | 100% | 100% | 104% | 100% | 100% |
| | Lidocaine | (Normialized) | 2.03% | 2.03% | 2.10% | 2.07% | 2.11% |
| | | | 100% | 100% | 103% | 102% | 104% |

In the above Table 3, the six (6)-month accelerated stability assay data's for both formulations, i.e. Example 8 and Example 9 (containing BHT) were stable.

TABLE 4

Stability data of Sorivudine/lidocaine cream formulas of Examples 3, 4 and 5 stored in 40° C./75% RH

| Formula | Drug | | 0 (initial) | 1 month | 2 month | 3 month | 6 month |
|---|---|---|---|---|---|---|---|
| Example 10 (pH 5.4) | Sorivudine | (normalized) | 2.39% | 2.30% | 2.18% | 2.15% | 2.05% |
| | | | 100% | 96% | 91% | 90% | 86% |
| | Lidocaine | (normalized) | 4.05% | 4.05% | 4.09% | 4.15% | 4.02% |
| | | | 100% | 100% | 101% | 102% | 99% |
| Example 11 (pH 7.3) | Sorivudine | (normalized) | 2.30% | 2.00% | 1.85% | 1.45% | 1.04% |
| | | | 100% | 87% | 80% | 63% | 45% |
| | Lidocaine | (normalized) | 3.98% | 4.04% | 3.97% | 4.05% | 3.82% |
| | | | 100% | 101% | 100% | 102% | 96% |
| Example 12 (pH 9.1) | Sorivudine | (normalized) | 2.37% | 1.56% | 1.30% | 0.93% | 0.42% |
| | | | 100% | 66% | 55% | 39% | 18% |
| | Lidocaine | (normalized) | 3.81% | 3.78% | 3.79% | 3.84% | 3.28% |
| | | | 100% | 99% | 99% | 101% | 86% |

Examples 10, 11 and 12 were provided with sorivudine dissolved in propylene glycol and PEG400. Table 4 shows that lidocaine HCl was stable in all of the different pH environments, i.e., Example 10—acidic (pH5.4), Example 11—neutral (pH7.3) or Example 12—basic (pH9.1). However, sorivudine was not stable in all of the three different pH environments. For example, in the acidic environment of composition of Example 10, the 6 month accelerated results showed that the amount of sorivudine dropped to 86%.

Further, sorivudine was not stable in a dissolved system. When comparing Example 14 (dispersed system), as provided below in Table 5, with Example 12 (dissolved system), sorivudine is found to be more stable in a dispersed system than in the dissolved system. This is because in the dissolved system of Example 12, sorivudine was mainly dissolved in PEG400 and Propylene glycol, and thus exposed to degradation.

As provided in Table 3 above, sorivudine in both Examples 8 and 9 were mainly finely dispersed in the cream system, i.e. sorivudine was not dissolved and was only dispersed in the system, thereby showing better stability.

Moreover, Example 10, 11 and 12 showed that the higher the pH the more unstable sorivudine is. A basic pH environment affects the stability of sorivudine.

TABLE 5

Stability data of Sorivudine/lidocaine cream formulas of Examples 13, 14 and 15 stored in 40° C./75% RH

| Formula | Drug | | 0 (initial) | 1 month | 2 month | 3 month | 6 month |
|---|---|---|---|---|---|---|---|
| Example 13 (pH 7.1) | Sorivudine | (normalized) | 3.22% | 3.06% | 2.94% | 2.63% | 2.14% |
| | | | 100% | 95% | 91% | 82% | 66% |
| | Lidocaine | (normalized) | 2.19% | 2.11% | 1.93% | 2.10% | 2.16% |
| | | | 100% | 96% | 88% | 96% | 99% |

TABLE 5-continued

Stability data of Sorivudine/lidocaine cream formulas of
Examples 13, 14 and 15 stored in 40° C./75% RH

| Formula | Drug | 0 (initial) | 1 month | 2 month | 3 month | 6 month |
|---|---|---|---|---|---|---|
| Example 14 (pH 4.29) | Sorivudine (normalized) | 3.13% 100% | 2.91% 93% | 3.11% 99% | 3.13% 100% | 3.15% 101% |
|  | Lidocaine (normalized) | 2.15% 100% | 2.04% 95% | 2.11% 98% | 2.11% 98% | 2.16% 101% |
| Example 15 (pH 4.27) | Sorivudine (normalized) | 3.15% 100% | 3.18% 101% | 3.09% 98% | 3.15% 100% | 3.03% 96% |
|  | Lidocaine (normalized) | 2.14% 100% | 2.16% 101% | 2.11% 98% | 2.16% 101% | 2.22% 103% |

Table 5 shows that Lidocaine HCl is stable in both acidic (pH 4.29—Example 14) and neutral environments (pH 7.1—Example 13). Sorivudine cream of Example 14, which has a pH of 4.29, shows that sorivudine is stable in contrast to the sorivudine in the formulation of Example 13, which has a pH of 7.1. This shows that sorivudine is more stable in an acidic environment (pH4.29) than in a neutral environment (pH7.1).

In the neutral environment, the assay of sorivudine remained only 66% while lidocaine HCl had almost no change at 6 month of this accelerated test. In acidic environment, both sorivudine and lidocaine HCl showed no change.

Examples 18-22

The cream formulations of Examples 18-22 were prepared as follows:

Example 18

D1811, Tween80, span80, glycerol were dissolved in ethanol at 60° C. to obtain Solution 1. Lidocaine HCl was dissolved in purified water and then added into Solution 1 to provide Solution 2. Cetylalcohol, octadecanol, caprylic/capric triglyceride (CCT), glyceryl monostearate (GM) and dimethicone were melted at 80° C. to obtain Oil phase 1. Solution 2 was mixed and emulsified with Oil phase 1 to obtain a cream. Sorivudine was slowly dispersed and emulsified into the cream.

Example 19

D1811, Tween80, span80, glycerol were dissolved in ethanol at 60° C. to obtain Solution 1. Lidocaine HCl was dissolved in purified water and then added into Solution 1 to provide Solution 2. Cetylalcohol, octadecanol, CCT, GM, BHT and dimethicone were melted at 80° C. to obtain Oil phase 2. Solution 2 was mixed and emulsified with Oil phase 2 to obtain a cream. Sorivudine was slowly dispersed and emulsified into the cream.

Example 20

D1811, Tween80, span80, glycerol were dissolved in ethanol at 60° C. to obtain Solution 1. Lidocaine HCl was dissolved in Carbomer 980 solution to obtain Solution 3. Sorivudine was dissolved in PG and PEG400 and mixed with Solution 1 and Solution 3 to obtain Aqueous Solution 4. Cetylalcohol, octadecanol, CCT, GM, Sodium sulfite and dimethicone were melted at 80° C. to obtain Oil phase 3. Aqueous solution 4 was mixed and emulsified with Oil phase 3 to obtain a cream. Peppermint oil was slowly added to the cream and the cream was emulsified.

Examples 21-22

D1811, Tween80, span80, glycerol were dissolved in ethanol at 60° C. to obtain Solution 1. Lidocaine HCl was dissolved in purified water and then added into Solution 1 to provide Solution 2. Cetylalcohol, octadecanol, CCT, GM, BHT and dimethicone were melted at 80° C. to obtain Oil phase 2. Solution 2 was mixed and emulsified with Oil phase 2 to obtain a cream. Sorivudine was slowly dispersed and emulsified into the cream.

The compositions of Examples 18-22 are listed in Table 6.

TABLE 6

Compositions of Sorivudine-Lidocaine cream formulations

| Ingredients | Ex 18 | Ex 19 | Ex 20 | Ex 21 | Ex 22 |
|---|---|---|---|---|---|
| Sorivudine | 3.00% | 3.00% | 3.00% | 3.00% | 3.00% |
| Lidocaine HCl | 2.00% | 2.00% | 4.00% | 2.00% | 5.00% |
| D1811 | 0.50% | 0.50% | 0.50% | 0.50% | 0.50% |
| Tween 80 | 0.25% | 0.25% | 0.50% | 0.25% | 0.25% |
| Span80 | 0.25% | 0.25% | 0.50% | 0.25% | 0.25% |
| Glycerol | 3.00% | 3.00% | — | 3.00% | 3.00% |
| Ethanol | 8.00% | 8.00% | — | 3.00% | 3.00% |
| Cetylalcohol | 3.00% | 3.00% | 1.50% | 3.00% | 3.00% |
| Octadecanol | 3.00% | 3.00% | 1.50% | 3.00% | 3.00% |
| PG* | — | — | 10.0% | — | — |
| PEG 400 | — | — | 20.0% | — | — |
| Benzoic acid | — | — | 2.00% | — | — |
| CCT* | 2.00% | 2.00% | 3.00% | 2.00% | 2.00% |
| GM* | 5.00% | 5.00% | 5.00% | 5.00% | 5.00% |
| Dimethicone | 2.00% | 2.00% | 2.00% | 2.00% | 2.00% |
| Carbomer 980 | — | — | 0.20% | — | — |
| BHT | — | 0.50% | — | 0.10% | 0.10% |
| Sodium sulfite | — | — | 0.50% | — | — |
| Peppermint oil | — | — | 0.50% | — | — |
| Purified water | QS | QS | QS | QS | QS |

*PG: propylene glycol, CCT: caprylic/capric triglyceride, GM: glyceryl monostearate It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

We claim:

1. A pharmaceutical composition for topical administration consisting of:
   an antiviral drug which is sorivudine,
   a local anesthetic selected from the group consisting of lidocaine and its pharmaceutically acceptable salt,
   sucrose stearate,
   polysorbate 80,
   sorbitan monooleate,
   glycerol,
   ethanol,
   water,
   cetylalcohol,
   octadecanol,
   caprylic capric triglyceride,
   dimethicone, and
   glyceryl monostearate,
   wherein the range of the antiviral drug sorivudine is from about 1% to about 5% w/wt, wherein the range of the local anesthetic lidocaine and its pharmaceutically acceptable salt is from about 1% to about 6% wt/wt, and wherein the pH of the composition is from about 4.0 to about 4.5.

2. The pharmaceutical composition of claim 1, wherein the range of the antiviral drug sorivudine is from about 2% to about 4% wt/wt.

3. The pharmaceutical composition of claim 1, wherein the range of the local anesthetic lidocaine and its pharmaceutically acceptable salt is from about 2% to about 5% wt/wt.

4. The pharmaceutical composition of claim 1, wherein the antiviral drug is sorivudine 5% and the local anesthetic is lidocaine 5%; the antiviral drug is sorivudine 3% and the local anesthetic is lidocaine 5%; or the antiviral drug is sorivudine 3% and the local anesthetic is lidocaine 2%.

5. A cream, lotion, gel or ointment, solution, liniment, suspension, lacquer, spray, a topical patch, transdermal patch, hydrogel patch, matrix patch, reservoir patch, electrophoresis patch or micro-needle patch containing a pharmaceutical composition of claim 1.

6. A method for treating herpes virus infections of the skin and pain associated therewith comprising topically applying the pharmaceutical composition of claim 1.

* * * * *